(12) United States Patent
Yoshioka et al.

(10) Patent No.: US 7,982,458 B2
(45) Date of Patent: Jul. 19, 2011

(54) WIRE-ROPE FLAW DETECTOR

(75) Inventors: Takashi Yoshioka, Tokyo (JP); Hiroshi Sasai, Tokyo (JP); Yoshinori Miyamoto, Tokyo (JP)

(73) Assignee: Mitsubishi Electric Corporation, Chiyode-Ku, Tokyo (JP)

( * ) Notice: Subject to any disclaimer, the term of this patent is extended or adjusted under 35 U.S.C. 154(b) by 291 days.

(21) Appl. No.: 12/421,677

(22) Filed: Apr. 10, 2009

(65) Prior Publication Data

US 2010/0182000 A1 Jul. 22, 2010

(30) Foreign Application Priority Data

Jan. 22, 2009 (JP) ................................. 2009-012025

(51) Int. Cl.
*G01N 27/82* (2006.01)
*G01R 33/12* (2006.01)
*G01R 31/28* (2006.01)

(52) U.S. Cl. .......................... 324/240; 324/228; 324/529

(58) Field of Classification Search .................. 324/240, 324/239, 228, 200, 260, 262, 241–243, 76.11, 324/144, 331, 345, 529, 117 R; 336/214, 336/215, 220–222, 173, 233, 30

See application file for complete search history.

(56) References Cited

U.S. PATENT DOCUMENTS

| 4,427,940 A * | 1/1984 | Hirama et al. ................. 324/240 |
| 2010/0019762 A1 | 1/2010 | Furusawa et al. |
| 2010/0102807 A1 | 4/2010 | Yoshioka et al. |
| 2011/0006762 A1 * | 1/2011 | Yoshioka et al. ............. 324/240 |

FOREIGN PATENT DOCUMENTS

| JP | 55-094156 | 7/1980 |
| JP | 56-044840 | 4/1981 |
| JP | 05-043605 | 2/1993 |
| JP | 09-145678 A | 6/1997 |
| JP | 09-210968 A | 8/1997 |
| JP | 2001-041933 | 2/2001 |
| JP | 2005-089172 | 4/2005 |
| JP | 2005-106602 | 4/2005 |
| WO | WO 2008/093409 | 8/2008 |
| WO | WO 2008/093410 | 8/2008 |

OTHER PUBLICATIONS

Office Action dated Nov. 16, 2010, issued in the corresponding Japanese Patent Application No. 2009-012025.

* cited by examiner

*Primary Examiner* — Hoai-An D Nguyen
(74) *Attorney, Agent, or Firm* — Buchanan Ingersoll & Rooney PC

(57) ABSTRACT

There is obtained a wire-rope flaw detector capable of realizing a high signal-to-noise ratio even in the case where only one detection coil is disposed. In the wire-rope flaw detector, there are provided a magnetizer that forms main magnetic flux in a predetermined section located along an axis direction of a wire rope (1) and a detection coil (8) that detects, in the predetermined section, leakage magnetic flux (13) emitted from a flaw portion (10) of the wire rope (1); a magnetic circuit member (7) made of a ferromagnetic material intervenes in a magnetic circuit for leakage magnetic flux that is interlinked with a detection coil (8); and in a space where at least one of the end portions, of the magnetic circuit member (7), that serve as the inflow port and the outflow port for the leakage magnetic flux is inserted between the detection coil (8) and a wire rope (1), an opening portion extends in such a way as to intervene between the foregoing end portion and the other end portion and is inserted between the detection coil (8) and the wire rope (1).

6 Claims, 22 Drawing Sheets

\* IN DEGREES

|  | FIRST (FUNDAMENTAL WAVE) | THIRD | FIFTH | SEVENTH |
|---|---|---|---|---|
| MAGNETIC CIRCUIT MEMBER WITH FOLDED NAILS | 0 | 180 | 0 | 180 |
| NO MAGNETIC CIRCUIT MEMBER | 0 | 0 | 0 | 0 |
| E-SHAPED MAGNETIC CIRCUIT MEMBER | 0 | 0 | 0 | 0 |

Fig. 13

WIRE-ROPE FLAW DETECTOR

BACKGROUND OF THE INVENTION

1. Field of the Invention

The present invention relates to a wire-rope flaw detector that detects strand breakage and breakage of a wire rope (referred to as a wire-rope flaw portion, hereinafter) for suspending a car such as an elevator car.

2. Description of the Related Art

To date, a wire-rope flaw detector has been configured with excitation iron cores, each having at least two magnetic poles, that are arranged in such a way as to face a wire rope and spaced close to each other, respective excitation permanent magnets embedded in the excitation iron cores, and a detection coil disposed at a place between the two magnetic poles; by magnetically saturating the wire rope by means of the two magnetic poles, magnetic flux is generated at a portion of a flaw such as a strand breakage, and by detecting the magnetic flux with the detection coil, the wire-rope flaw portion is detected; there exists a technology in which two detection coils are arranged spaced a predetermined distance apart from each other, and by making subtraction between the outputs of the detection coils, commonly superimposed noise is cancelled so as to raise the signal-to-noise ratio.

In a wire-rope flaw detector disclosed in Japanese Patent Application Laid-Open No. H9-210968, two detection coils are utilized in order to raise the signal-to-noise ratio. The amount of leakage magnetic flux emitted from a flaw portion is far smaller than the amount of the main magnetic flux that saturates the whole rope, and the distribution range thereof is limited to a space in the vicinity of the flaw portion. On the other hand, the voltage, across the detection coil, induced by a constant amount of interlink magnetic flux is in proportion to the number of coil turns. However, even though the coil is disposed in a region where no leakage magnetic flux is distributed, no effective interlink magnetic flux is obtained; therefore, the size of the coil is limited to be the same as or smaller than a certain size (a certain size is a value that depends on the wire-rope diameter and the wire-rope strand diameter). It is an important point in designing the coil that the number of turns is made as large as possible, with the coil size the same as or larger than the certain size; therefore, as a wire material used for the detection coil, an ultrafine electric wire having a diameter of several tens of micrometers is utilized. Additionally, in order to extend a wire-rope flaw portion detectable range, these coils tend to be formed bent in such a way as to enfold a rope.

In order to wind the ultrafine electric wire without causing any winding unevenness and to form it in an approximately U shape without breaking it, there are required dedicated apparatuses or jigs, worker who have learned the skill, and a certain working time; as a result, the coil becomes a component, whose production cost is relative high, among the components that configure the wire-rope flaw detector. Accordingly, arranging two detection coils, as the wire-rope flaw detector disclosed in Japanese Patent Application Laid-Open No. H9-210968, in order to raise the signal-to-noise ratio, becomes one of the factors that raise the production cost of the wire-rope flaw detector; thus, it has been a problem to reduce the cost. Additionally, arranging two detection coils makes the longitudinal dimension of the wire-rope flaw detector extend, and hence it is one of the factors that hinder the downsizing.

SUMMARY OF THE INVENTION

The present invention has been implemented in order to solve the foregoing problems; the objective thereof is to obtain a wire-rope flaw detector capable of realizing a high signal-to-noise ratio even in the case where only one detection coil is disposed.

A wire-rope flaw detector according to the present invention is provided with a magnetizer that forms main magnetic flux in a predetermined section located along an axis direction of a wire rope and a detection coil that detects, in the predetermined section, leakage magnetic flux emitted from a flaw portion of the wire rope; the wire-rope flaw detector has a structure in which a magnetic circuit member made of a ferromagnetic material intervenes in a magnetic circuit for leakage magnetic flux that is interlinked with a detection coil; and in a space where at least one of the end portions, of the magnetic circuit member, that serve as the inflow port and the outflow port for the leakage magnetic flux is inserted between the detection coil and a wire rope, an opening portion extends in such a way as to intervene between the foregoing end portion and the other end portion and is inserted between the detection coil and the wire rope.

A wire-rope flaw detector according to the present invention has a structure in which, in a space where at least one of the end portions, of a magnetic circuit member, that serve as the inflow port and the outflow port for leakage magnetic flux is inserted between a detection coil and a wire rope, an opening portion extends in such a way as to intervene between the foregoing end portion and the other end portion and is inserted between the detection coil and the wire rope; therefore, the respective amplitudes of harmonic components included in the waveform of a voltage induced across the detection coil become large, and the harmonic components keep a certain phase relationship with the fundamental wave. As a result, the waveform of a voltage generated due to a flaw can be characterized to some extent, whereby a flaw detection with a high signal-to-noise ratio can be realized even in the case where only one detection coil is disposed.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 13 is a table representing the results of frequency analyses on the waveforms in FIG. 12;

DETAILED DESCRIPTION OF THE INVENTION

Embodiment 1

Figure 1:
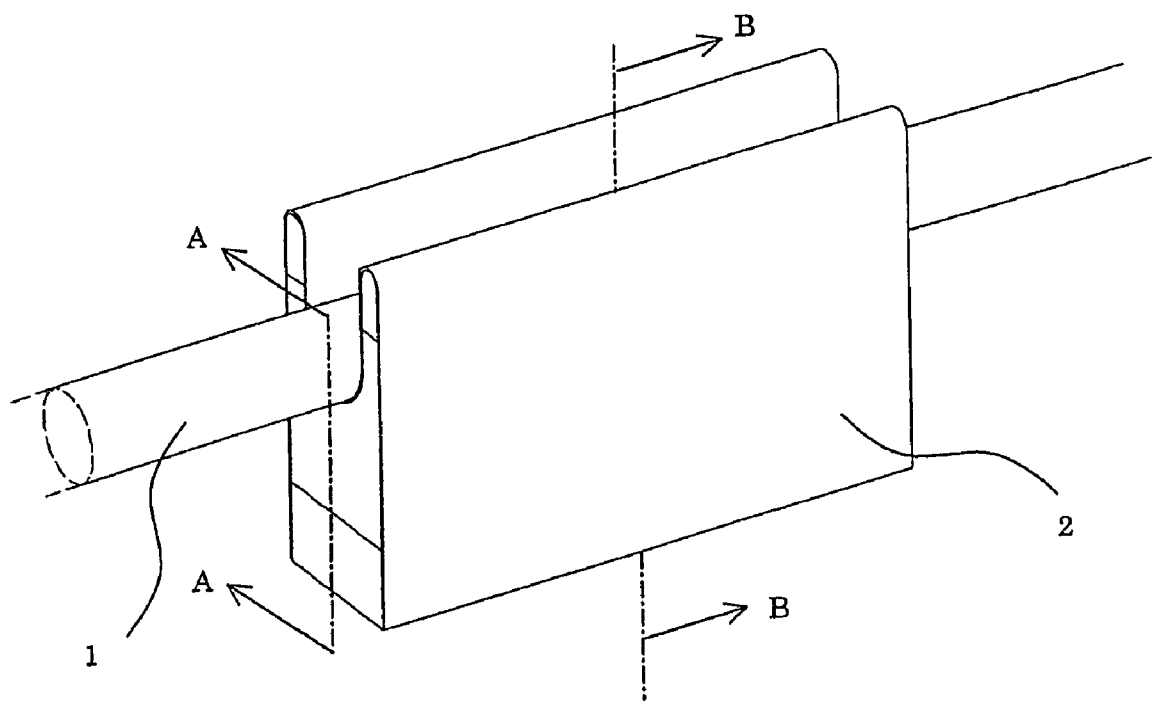
FIG. 1 is a perspective view illustrating the appearance of a wire-rope flaw detector according to Embodiment 1 of the present invention.
Figure 2:
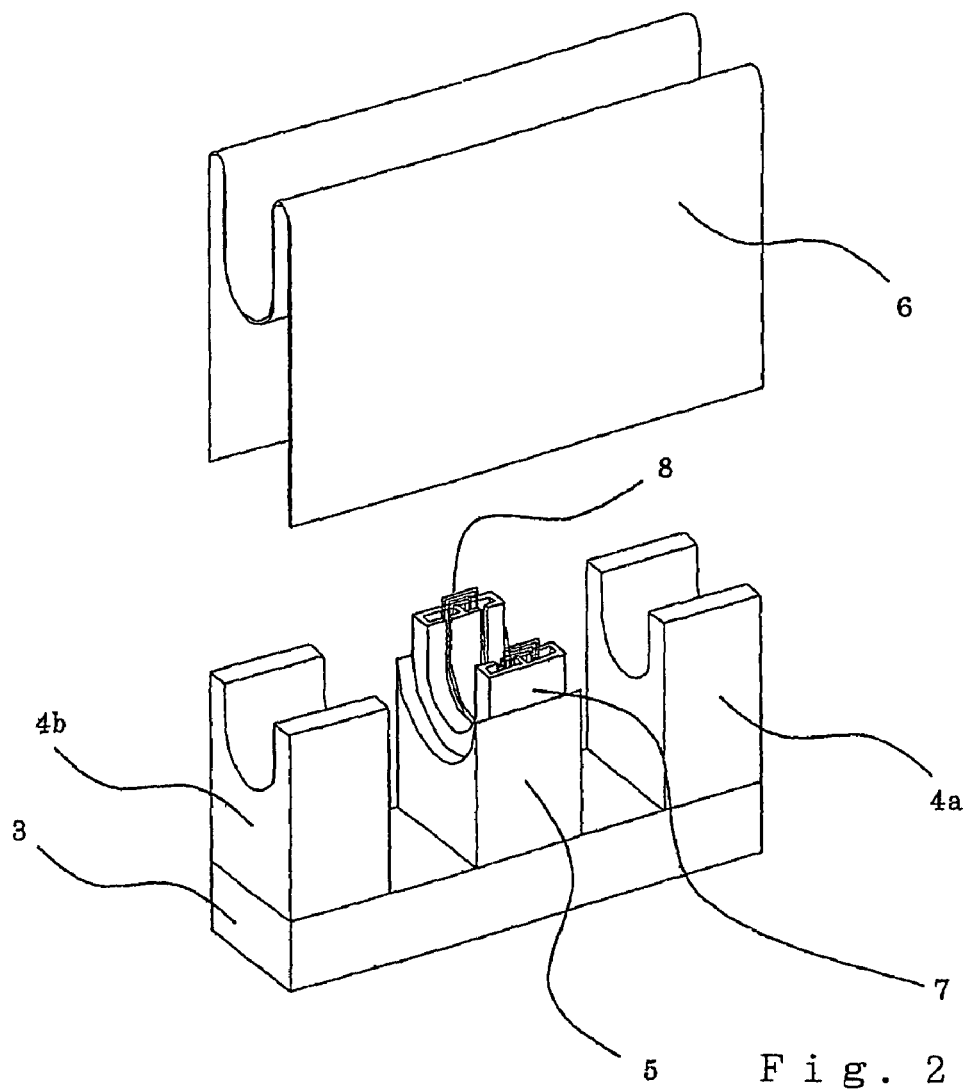
FIG. 2 is an exploded perspective view illustrating the appearance of the wire-rope flaw detector in FIG. 1 in the case where a protective plate is removed.

A wire-rope flaw detector according to Embodiment 1 of the present invention will be explained with reference to FIGS. 1 to 14. FIG. 1 is a perspective view illustrating the appearance of a wire-rope flaw detector according to Embodiment 1 of the present invention. Hereinafter, the same reference characters in the figures indicate the same or equivalent constituent elements. In FIG. 1, a wire rope 1 and a wire-rope flaw detector 2 are illustrated. FIG. 2 is an exploded perspective view illustrating the appearance of the wire-rope flaw detector in FIG. 1 in the case where a protective plate 6 is removed. In FIG. 2, there are illustrated a back yoke 3, an excitation permanent magnets 4a and 4b, a supporting base 5, the protective plate 6 removed from the wire-rope flaw detector, a magnetic circuit member 7, and a detection coil 8. A magnetizer of the wire-rope flaw detector 2 is to form a main magnetic circuit in a predetermined section of the wire rope 1; the magnetizer is configured with the back yoke 3 made of a ferromagnetic material and a pair of the excitation permanent magnets 4a and 4b that are arranged on the respective end portions of the back yoke 3 in such a way that the polarities thereof are opposite to each other.

Figure 3:
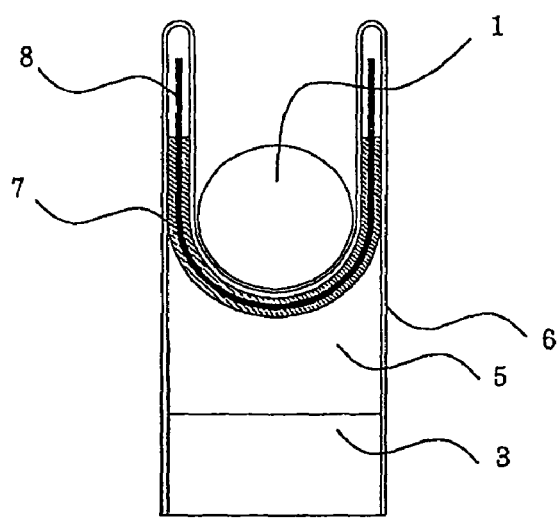
FIG. 3 is a cross-sectional view of the wire-rope flaw detector, as viewed along the line B-B in FIG. 1.

FIG. 3 is a cross-sectional view of the wire-rope flaw detector, as viewed along the line B-B in FIG. 1.

Figure 4:
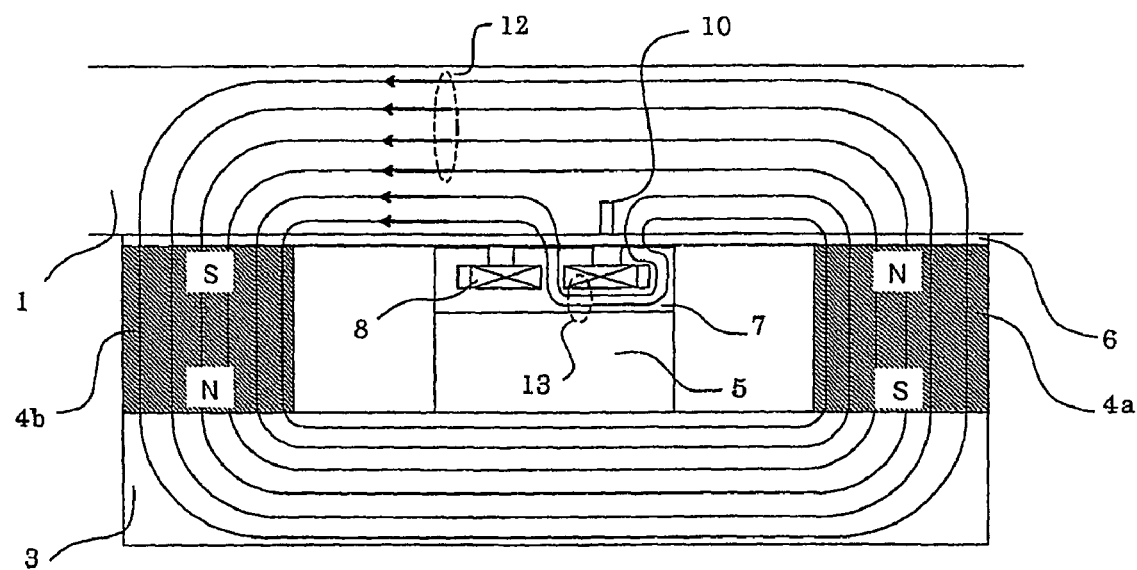
FIG. 4 is a configuration diagram of the wire-rope flaw detector, as viewed along the line A-A in FIG. 1; the configuration diagram illustrates the flow of magnetic flux in the vicinity of a flaw portion in the wire rope in the case where the wire-rope flaw detector is sliced along a plane including the center axis of the wire rope.

FIG. 4 is a configuration diagram of the wire-rope flaw detector, as viewed along the line A-A in FIG. 1; the configuration diagram illustrates the flow of magnetic flux in the vicinity of a flaw portion in the wire rope 1 in the case where the wire-rope flaw detector is sliced along a plane including the center axis of the wire rope 1. In FIG. 4, there are illustrated the wire rope 1, the back yoke 3, the excitation permanent magnets 4a and 4b, the supporting base 5, the magnetic circuit member 7, the detection coil 8, a flaw portion 10, main magnetic flux 12, and leakage magnetic flux 13. A flaw detection unit of the wire-rope flaw detector 2 is configured with the magnetic circuit member 7 and the detection coil 8.

Figure 5:
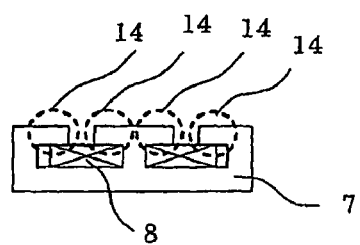
FIG. 5 is a cross-sectional view illustrating a magnetic circuit member and a detection coil in a flaw detection unit according to Embodiment 1.
Figure 6:
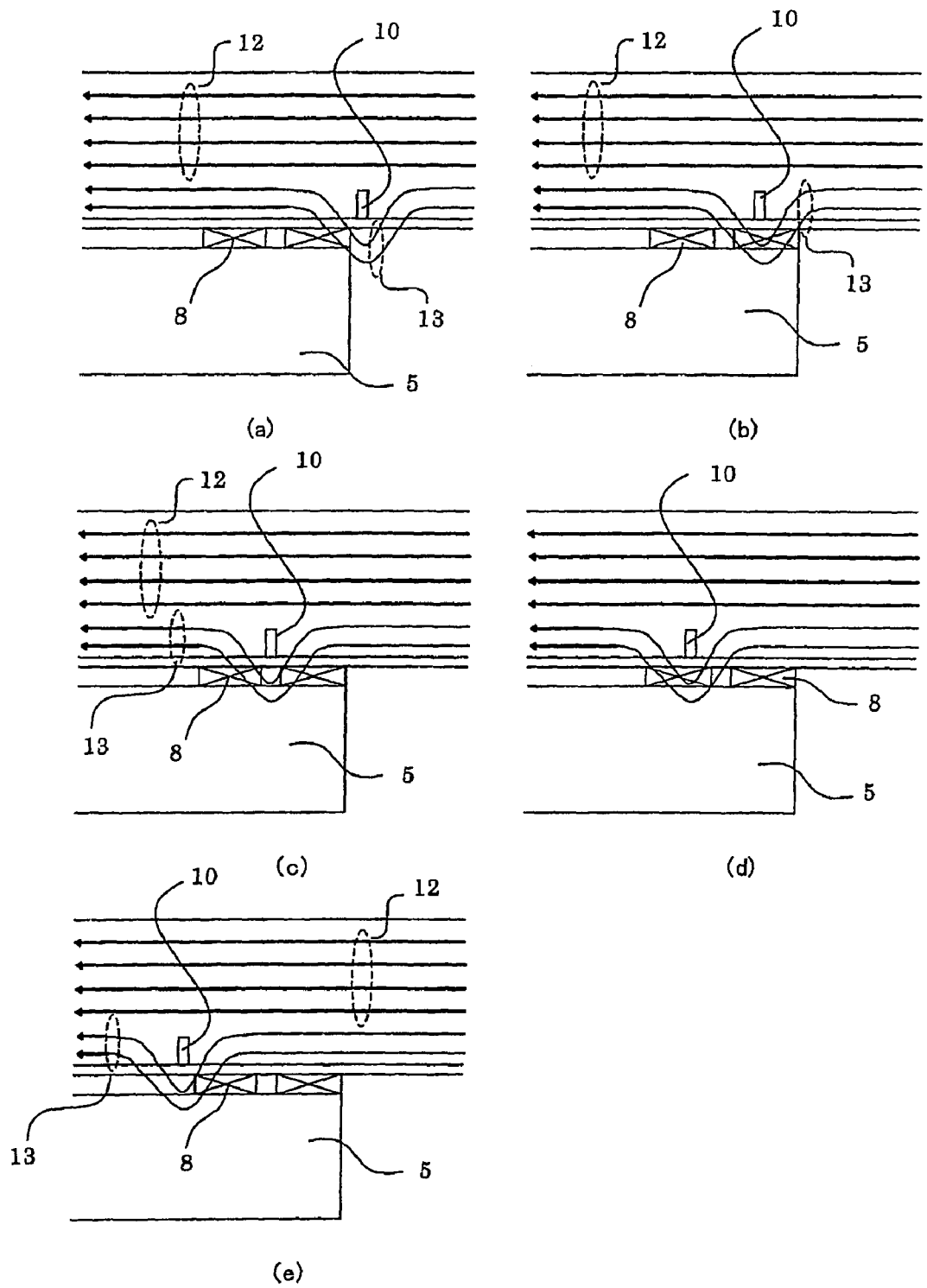
FIG. 6 is an explanatory diagram for explaining the manner in which leakage magnetic flux flows when a flaw portion passes by the vicinity of a flaw detection unit, in Japanese Patent Application Laid-Open No. H9-210968.
Figure 7:
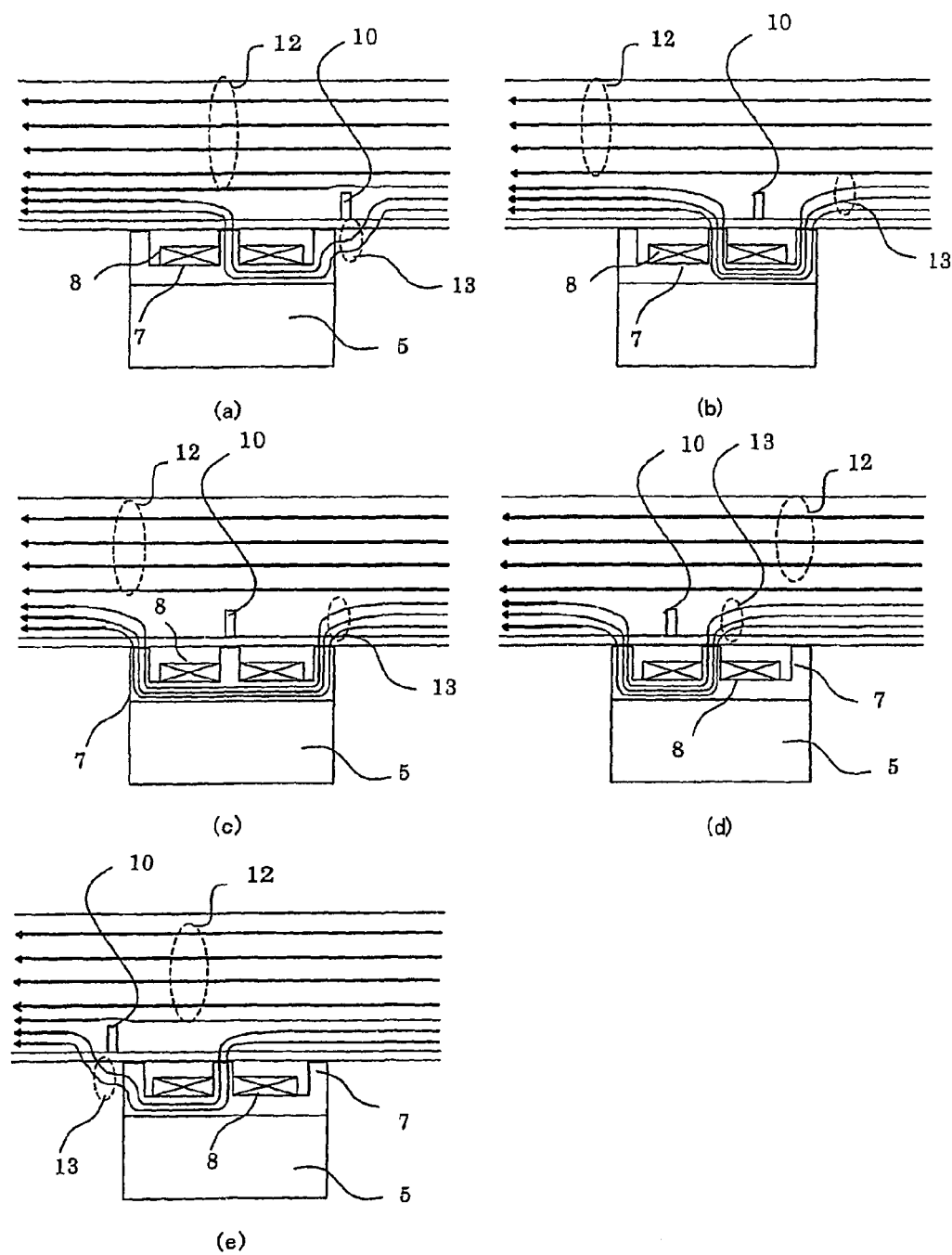
FIG. 7 is an explanatory diagram for explaining the manner in which leakage magnetic flux flows when a flaw portion passes by the vicinity of a flaw detection unit, in Japanese Patent Application Laid-Open No. H9-145678.
Figure 8:
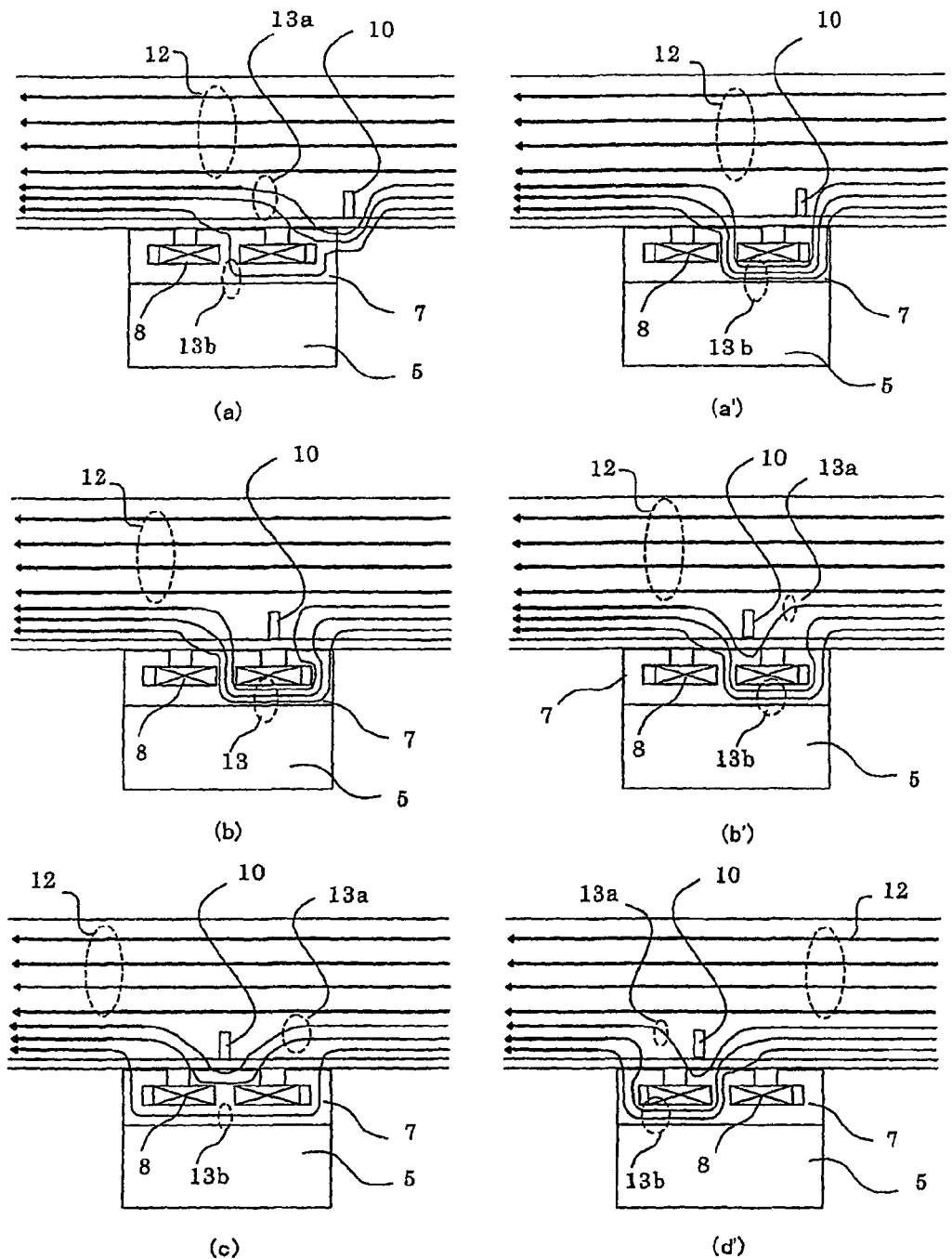
FIG. 8 is an explanatory diagram for explaining the manner, in Embodiment 1, in which leakage magnetic flux flows when a flaw portion passes by the vicinity of a flaw detection unit.
Figure 9:
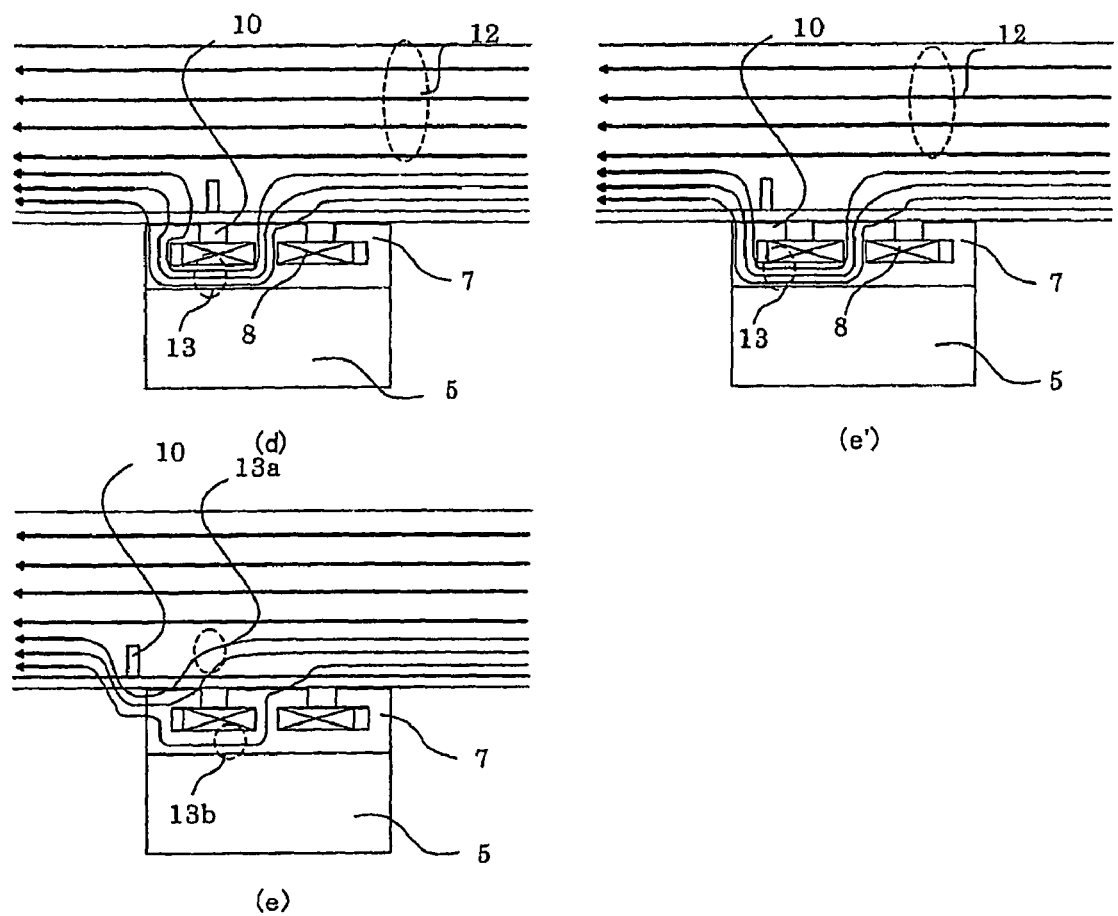
FIG. 9 is an explanatory diagram for explaining the manner, in Embodiment 1, in which leakage magnetic flux flows when a flaw portion passes by the vicinity of a flaw detection unit.
Figure 10:
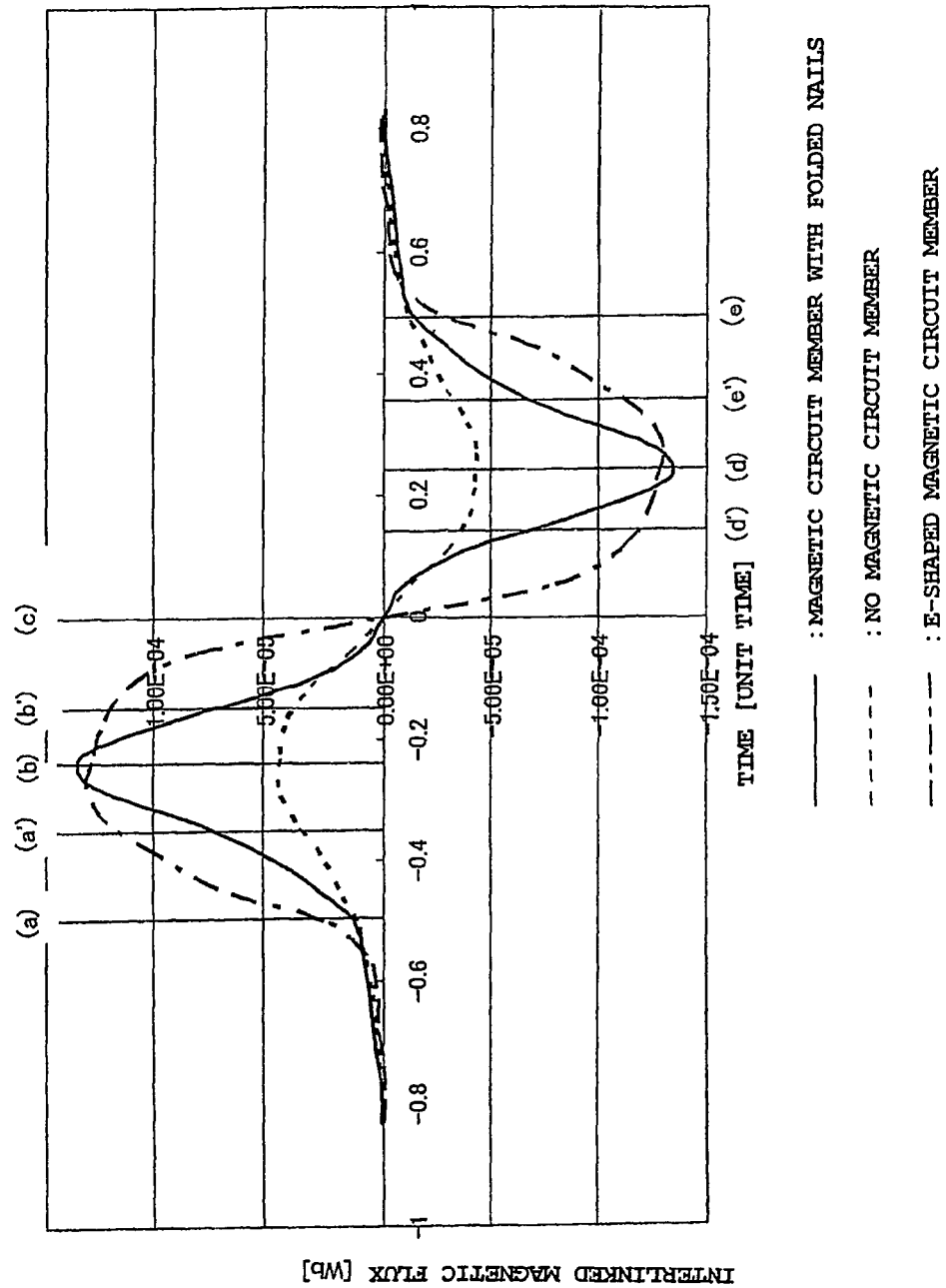
FIG. 10 is a waveform chart representing the amount of magnetic flux that is interlinked with the detection coil in the case where the flaw portion in FIGS. 6 to 9 is located at any one of positions (a) to (e)

FIG. 5 is a cross-sectional view illustrating the magnetic circuit member 7 and the detection coil 8 in the flaw detection unit according to Embodiment 1. In Embodiment 1, the magnetic circuit member 7 has folded nail portions 14 in such a way as to almost cover the detection coil on a plane that faces the wire rope, excluding opening portions which are part of the magnetic circuit member 7. In Japanese Patent Application Laid-Open No. H9-210968 (conventional), FIG. 6 is an explanatory diagram for explaining the manner in which leakage magnetic flux flows when a flaw portion 10 passes by the vicinity of a flaw detection unit; in Japanese Patent Application Laid-Open No. H9-145678 (conventional), FIG. 7 is an explanatory diagram for explaining the manner in which leakage magnetic flux flows when a flaw portion 10 passes by the vicinity of a flaw detection unit. In Embodiment 1, FIGS. 8 and 9 are each an explanatory diagram for explaining the manner in which leakage magnetic flux flows when the flaw portion 10 passes by the vicinity of the flaw detection unit; parts (a) to (d') of FIG. 8 and parts (d) to (e) of FIG. 9 are explanatory diagrams in series. FIG. 10 is a waveform chart representing the amount of magnetic flux that is interlinked with the detection coil 8 in the case where the flaw portion 10 in FIGS. 6 to 9 is located at any one of positions (a) to (e).

Figure 11:
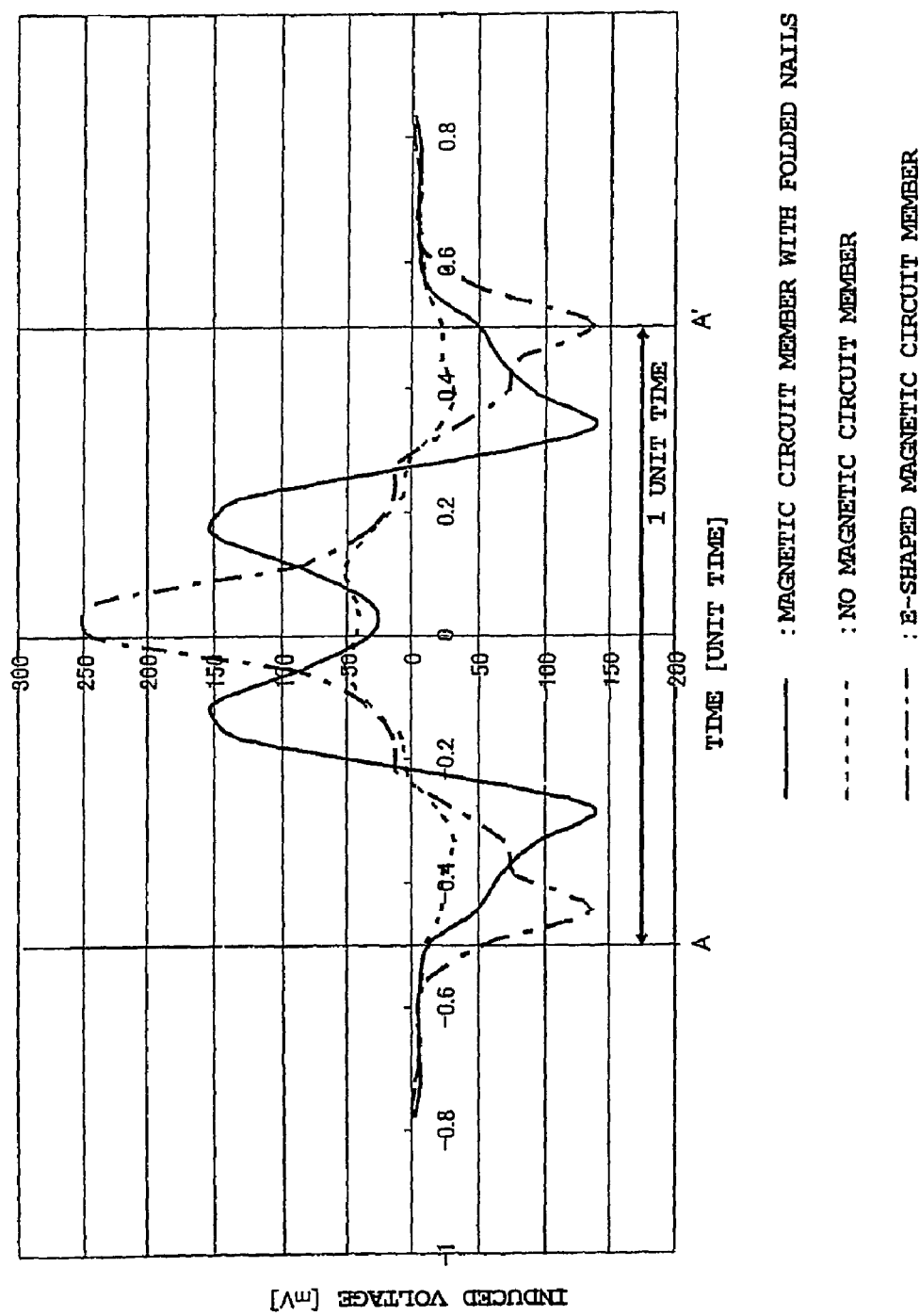
FIG. 11 is a waveform chart representing the waveforms of voltages induced across the detection coils in FIGS. 6 to 9.
Figure 12:
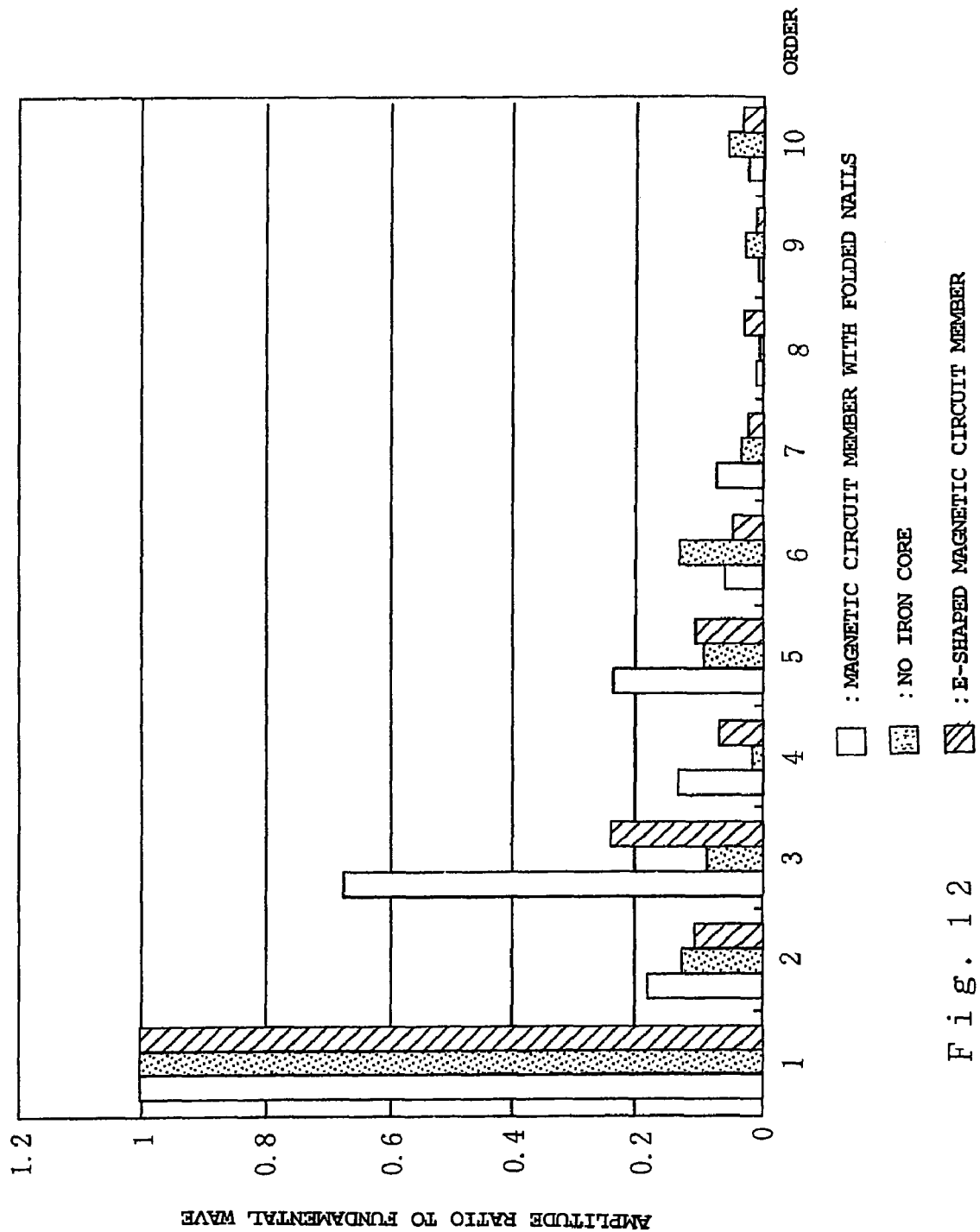
FIG. 12 is a graph representing the results of frequency analyses on the waveforms in FIG. 11.
Figure 14:
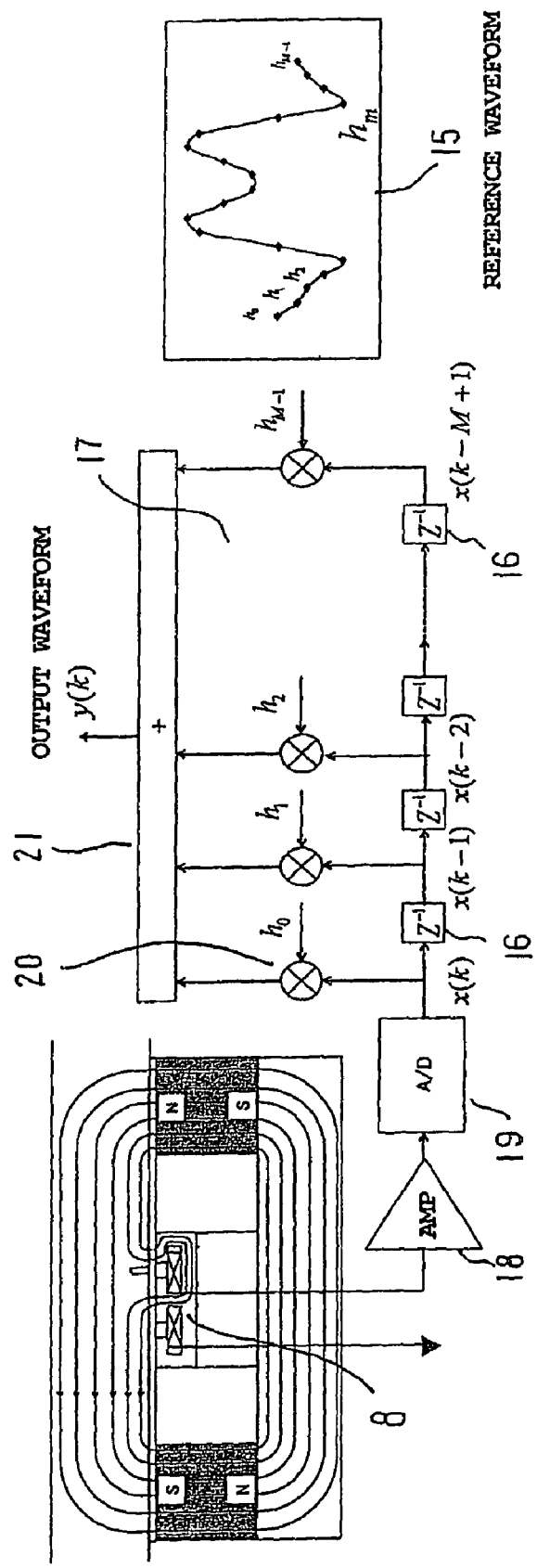
FIG. 14 is a block diagram illustrating a waveform detector according to Embodiment 1.

FIG. 11 is a waveform chart representing the waveform of a voltage induced across the detection coil 8 in FIGS. 6 to 8; the waveform is obtained by temporally differentiating the waveform, in FIG. 10, that represents the amount of magnetic flux and then reversing the polarity of the differentiated waveform. The unit time in FIG. 11 is a time in which the flaw portion 10 illustrated in FIGS. 6 to 10 travels from the position (a) to the position (e); the reason why the waveform in one unit time looks horizontally asymmetric is that the zero point in the abscissa is shifted from the peak position of the waveform; this asymmetry is caused by the shift of the temporal axis due to the differentiation. FIG. 12 is a graph representing the results of frequency analyses on the waveforms in FIG. 11. The fundamental frequency (=1) in FIG. 12 is the reciprocal of the unit time. FIG. 13 is a table representing the results of frequency analyses on the waveforms in FIG. 12; the unit is "degree". As represented in FIG. 13, in addition to the quantitative difference in the harmonic components, the phase is characterized compared to the conventional example. Because of both matters described above, there exists a characteristic wave form represented by the waveform for the magnetic circuit member having folded nails in FIG. 11. FIG. 14 is a block diagram illustrating a detector according to Embodiment 1.

Next, a wire-rope flaw detector according to Embodiment 1 will be explained with reference to the accompanying drawings. The wire-rope flaw detector 2 forms, by means of the magnetizer, a main magnetic circuit in a predetermined section along the axis direction of the wire rope 1. The magnetic circuit member 7 made of a ferromagnetic material is formed in such a way that the shape of a cross section thereof taken along the center axis of a wire rope has an opening in part of character "8"; excluding the opening, the magnetic circuit member 7 intervenes between the wire rope 1 and the detection coil 8. A part of the magnetic circuit member 7 that intervenes in a space between the wire rope 1 and the detection coil 8 will be referred to as a folded nail portion 14 for convenience. The magnetic circuit member 7 is disposed at a position that is equidistant from the excitation permanent magnets 4a and 4b. FIG. 3 is a cross-sectional view of the magnetic circuit member 7 taken along a plane that perpendicularly slices the wire rope 1; in order to widen the flaw detectable range, the magnetic circuit member 7 is formed in an approximately U shape.

Here, with reference to FIGS. 6 to 9, there will be explained a process in which the flaw portion 10 of the wire rope 1 approaches the flaw detection unit and magnetic flux is interlinked with the detection coil. At first, there will be explained the manner in which magnetic flux is interlinked with the detection coil 8 according to FIG. 6, i.e., Japanese Patent Application Laid-Open No. H9-210968. When, as illustrated in FIG. 6(a), part of the leakage magnetic flux 13 emitted from the flaw portion passes through an end portion of the detection coil 8, a voltage is induced only across the electric wires, among ring-shaped electric wires that configure the detection coil 8, with which the magnetic flux is interlinked. After that, the amount of the leakage magnetic flux that is interlinked with the electric wires gradually increases, and when the positional relationship between the leakage magnetic flux 13 and the detection coil 8 becomes as illustrated in FIG. 6(b), the amount of the magnetic flux that is interlinked with the detection coil 8 becomes maximum. When, after the leakage magnetic flux 13 further travels, the positional relationship between the leakage magnetic flux 13 and the detection coil 8 becomes as illustrated in FIG. 6(c), the amount of the magnetic flux that is interlinked with the detection coil 8 temporarily becomes zero; when, after the leakage magnetic flux 13 further travels, the positional relationship between the leakage magnetic flux 13 and the detection coil 8 becomes as illustrated in FIG. 6(d), the amount of the magnetic flux that is interlinked with the detection coil 8 again becomes maximum, but the polarity thereof is reversed; thereafter, as illustrated in FIG. 6(e), as the leakage magnetic flux 13 recedes from the detection coil 8, the amount of the leakage magnetic flux that is interlinked with the detection coil 8 decreases.

The broken line in FIG. 10 represents the foregoing circumstances in which the amount of interlinked magnetic flux changes. Similarly, FIGS. 7(a) to 7(e) illustrate the circumstances of leakage magnetic flux in the case where a magnetic circuit member having an E-shaped cross section, which is disclosed in Japanese Patent Application Laid-Open No. H9-145678, is utilized. Because of the intervention of a magnetic circuit member 7, which is a ferromagnetic material, the amount of interlinked magnetic flux largely increases, compared to the detection coil according to Japanese Patent Application Laid-Open No. H9-210968; however, the behavior of the change in the amount of interlinked magnetic flux becomes moderate compared to the detection coil according to Embodiment 1 described below. The dashed line in FIG. 10 represents the circumstances in which the amount of the interlinked magnetic flux changes, in the case where the magnetic circuit member having an E-shaped cross section is utilized. Here, there will be explained the manner in which magnetic flux is interlinked with the detection coil 8 in the wire-rope flaw detector 2 according to Embodiment 1. When, as illustrated in FIG. 8(a), part of the leakage magnetic flux 3 emitted from the flaw portion 10 passes through an end portion of the magnetic circuit member 7, there exist, as magnetic circuits for the leakage magnetic flux 13, a route 13b that is interlinked with the detection coil 8 and a route 13a that passes through the folded nail portion 14 and then returns to the wire rope 1 without being interlinked with the detection coil 8; therefore, the speed of the increase in the magnetic flux in the detection coil 8 is low compared to the speed in the case of Japanese Patent Application Laid-Open No. H9-145678. However, when, as illustrated in FIG. 8(a'), the leakage magnetic flux 13 travels and the flaw portion 10 approaches the opening portion of the magnetic circuit member 7, most of the leakage magnetic flux 13 takes the route 13b that is interlinked with the detection coil 8; therefore, the amount of magnetic flux that is interlinked with the detection coil 8 drastically increases.

After that, when the flaw portion 10 reaches a position that faces the opening portion of the magnetic circuit member 7, i.e., the position in FIG. 8(b), the amount of magnetic flux that is interlinked with the detection coil 8 becomes maximum. When the flaw portion 10 further travels and the positional relationship between the flaw portion 10 and the magnetic circuit member 7 becomes as illustrated in FIG. 8(b'), part of the leakage magnetic flux changes its route from the route 13b to the route 13a that passes through the folded nail portion 14; therefore, the amount of the interlinked magnetic flux drastically decreases; after that, when the flaw portion 10 reaches the center of the magnetic circuit member 7, i.e., the position illustrated in FIG. 8(c), the amount of the interlinked magnetic flux temporarily becomes zero. Thereafter, the foregoing process of change is repeated with the polarity of the magnetic flux reversed. When the flaw portion 10 passes by the position illustrated in FIG. 8(d') and then the positional relationship between the flaw portion 10 and the detection coil 7 becomes as illustrated in FIG. 9(d), the amount of the interlinked magnetic flux again becomes maximum, but the polarity thereof is reversed. After that, when the flaw portion 10 passes by the position illustrated in FIG. 9(e') and the leakage magnetic flux 13 recedes from the detection coil 8, part of the leakage magnetic flux changes its route from the route 13b to the route 13a that passes through the folded nail portion; therefore, the amount of the interlinked magnetic flux drastically decreases. The solid line in FIG. 10 represents the manner, in Embodiment 1, in which the amount of interlinked magnetic flux changes.

Across the detection coil 8, there is induced a voltage that is in proportion to the temporal differentiation of the amount of interlinked magnetic flux. In FIG. 11, there are represented respective induced voltage waveforms according to Japanese Patent Application Laid-Open No. H9-210968, Japanese Patent Application Laid-Open No. H9-145678, and Embodiment 1, in the case where the respective numbers of turns of the detection coils are equal to one another. As described above, the temporal change in the magnetic flux that is interlinked with the detection coil 8 of the wire-rope flaw detector 2 according to Embodiment 1 is steep compared to Japanese Patent Application Laid-Open No. H9-210968, or Japanese Patent Application Laid-Open No. H9-145678, due to the existence of the magnetic circuit member 7 having the folded nail portions 14, and the absolute value of the amount of the interlinked magnetic flux is large; therefore, the fluctuation of the voltage induced across the detection coil 8 of the wire-rope flaw detector 2 becomes drastic. FIG. 12 is a graph representing the respective amplitudes of frequency components included in each of the waveforms in FIG. 11; FIG. 13 is a table representing the relationship among the phases of frequency components at the time instant "0".

In Embodiment 1, the reciprocal of the time period from the time instant immediately before the flaw portion 10 reaches the flaw detection unit to the time instant when the flaw portion 10 has just passed by the flaw detection unit (from FIG. 6(*a*) to FIG. 9(*e*)) is regarded as the fundamental frequency, and the amplitude at the fundamental frequency is regarded as "1". As is clear from FIG. 12, in the waveform of the voltage induced across the detection coil 8 of the wire-rope flaw detector 2, the ratio of the high-order harmonic components to the fundamental wave is large in the case of Embodiment 1, compared to Japanese Patent Application Laid-Open No. H9-210968, or Japanese Patent Application Laid-Open No. H9-145678. The high-order harmonic components are generated due to the folded nail portions 14 of the magnetic circuit member 7, and the phase relationship between the high-order harmonic components and the fundamental wave is determined by the shape of the folded nail portion 14; thus, the waveform of the voltage that is induced across the detection coil 8 due to the passage of the flaw portion 10 can have characteristics that cannot be found in noise signals.

Accordingly, for the voltage that is induced across the detection coil 8 and is to be measured, there is prepared a reference waveform 15 in which the amplitude and phase relationship among the foregoing fundamental-frequency component and the harmonic components are reflected, and there is performed a detection on waveform correlation between the reference waveform 15 and the waveform of another signal, that is to say, a degree of correlation is outputted. As a result, a flaw detection insusceptible to noise components can be performed. The correlation waveform detection can be realized in such a manner that, as illustrated in FIG. 14, the waveform of the voltage induced across the detection coil 8 is amplified by an amplifier 18 and then is digitized by an A/D converter 19 so that x(k) is outputted; after the A/D converter 19, a transversal filter 17 utilizing a delay element 16 is provided as a waveform detector and $h_m$ of the reference wave form 15 is reflected in the filter coefficient thereof so that y(k) is outputted. In addition, reference numerals 20 and 21 denote a multiplier and an adder, respectively.

In this situation, the output waveform y(k) represented in FIG. 14 can be given by the following equation (k, m, and M are integers).

$$y(k) = \sum_{m=0}^{M-1} h_m x(k-m) \tag{1}$$

Because any waveform can be expressed as a sum of sinusoidal waves, x(k) can be represented by the following equation.

$$h_m = \sum_{p=1}^{\infty} H_p \cos\left(\frac{2\pi\tau}{T} pm + \phi_p\right) \tag{2}$$

$$x(k) = \sum_{q=0}^{\infty} E_q \cos\left(\frac{2\pi\tau}{T} qk + \Psi_q\right) \tag{3}$$

where $H_p \geqq 0$, $E_q \geqq 0$, p an q are each an integer, T is a fundamental period, $\tau$ is a sampling period, $\phi_p$ and $\psi_q$ are each an initial phase.

Before and after a wire-rope flaw portion has passed by the detection coil 8, the amount of leakage magnetic flux becomes 0; thus, the sum of data $h_m$ $$\left(\sum_{m=0}^{M-1} h_m\right)$$

on reference waveforms is 0.

Substituting (2) and (3) for equation (1), $$y(k) = \tag{4}$$

$$\sum_{m=0}^{M-1} \left\{\sum_{p=1}^{\infty} H_p \cos\left(\frac{2\pi\tau}{T} pm + \phi_p\right)\right\} \left\{\sum_{q=0}^{\infty} E_q \cos\left(\frac{2\pi\tau}{T} q(k-m)\right) + \Psi_q\right\}$$

Equation (4) represents a sum of the products of cosine functions; when M is sufficiently large and $\tau$ is sufficiently large compared to T, the term of p ($\neq$q) becomes close to 0, due to the nature of a sinusoidal wave.

$$\cos\left(\frac{2\pi\tau}{T} pm + \phi_p\right)\cos\left(\frac{2\pi\tau}{T} q(k-m) + \Psi_q\right) \tag{5}$$

When $\phi_p = \psi_q + 2n\pi$ (n:integer), equation (5) is equal to 1; when $\phi_p = \psi_q + \pi/2 + 2n\pi$, equation (5) is equal to 0; when $\phi_p = \psi_q + \pi + 2n\pi$, equation (5) is equal to −1.

Figure 15:
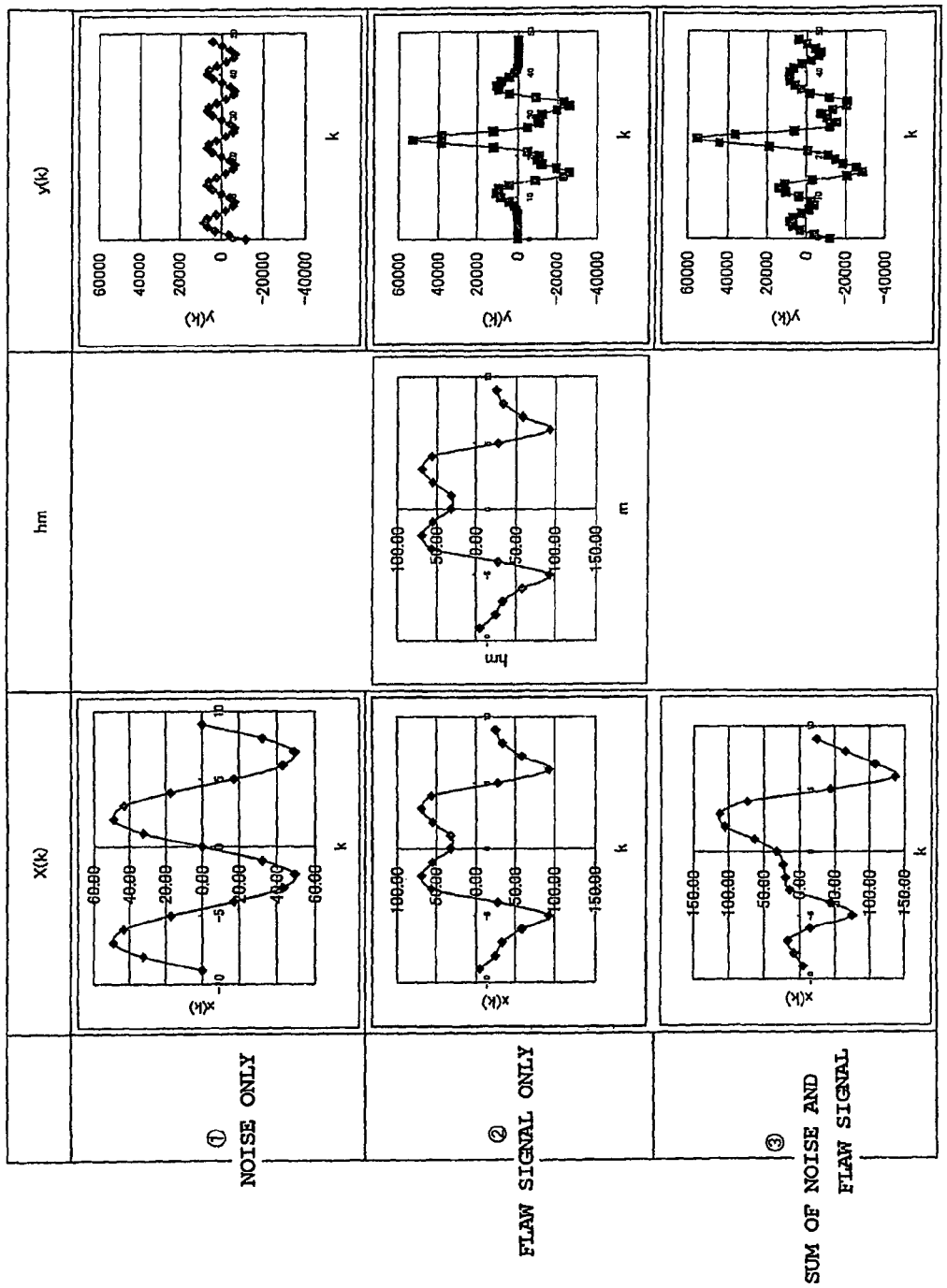
FIG. 15 is a set of charts representing the results of calculations, through Equation (1), of a noise signal that is different from a given reference waveform $h_m$, a flaw signal that is the same as the reference signal $h_m$, and the sum of the noise signal and the flaw signal.

In the case where p is equal to q, i.e., the result x(k) of sampling of a signal outputted from the detection coil 8 includes a frequency component and a phase component as the reference waveform $h_m$ has, the value of y(k) becomes a large positive value, but in other cases, y(k) becomes a small value; therefore, y(k) can be utilized as an index for measuring the similarity (a degree of correlation) between the reference waveform $h_m$ and x(k); in other words, a flaw signal can be detected. FIG. 15 is a set of charts representing the results of calculations, through Equation (1), of a noise signal that is different from a given reference waveform $h_m$, a flaw signal that is the same as the reference signal $h_m$, and the sum of the noise signal and the flaw signal. The unit of the ordinate of each chart in the column of y(k) of FIG. 15 is mV; values in mV are replaced by digitized numeral values. As illustrated in FIG. 14, it is made possible to extract only a voltage induced due to a flaw from the waveform x(k) of a voltage induced across the detection coil and to eliminate voltages induced due to noise, whereby a high signal-to-noise ratio can be realized only with a single coil.

As described above, a wire-rope flaw detector according to Embodiment 1 has a structure in which a magnetic circuit member made of a ferromagnetic material intervenes in a magnetic circuit for leakage magnetic flux that is interlinked with a detection coil; in a space where at least one of the end portions, of the magnetic circuit member, that serve as the inflow port and the outflow port for the leakage magnetic flux is inserted between the detection coil and a wire rope, an opening portion extends in such a way as to intervene between the foregoing end portion and the other end portion and is inserted between the detection coil and the wire rope. Accordingly, by attracting leakage magnetic flux emitted from a flaw portion by means of the extended magnetic circuit member (folded nail portion) and concentrating the timing when the leakage magnetic flux is interlinked with the detection coil in a certain time period, an induced voltage is characterized in such a way as to steeply change when the flaw portion passes by the detection coil, compared to a conventional wire-rope flaw detector having no folded nail portion. In other words, in addition to the fundamental wave component, harmonics components having large amplitude are superimposed on an induced voltage waveform. Either the frequency relationship or the phase relationship between the fundamental component and harmonics components is determined by the passage speed of the flaw portion and the shape of the magnetic circuit member and has characteristics that are not found in noise components superimposed on the induced voltage; therefore, by preparing a waveform detector having a reference waveform in which the characteristics are reflected and performing detection of correlation with the reference waveform, a high-S/N-ratio flaw detection can be realized without providing two detection coils.

Embodiment 2

Figure 16:
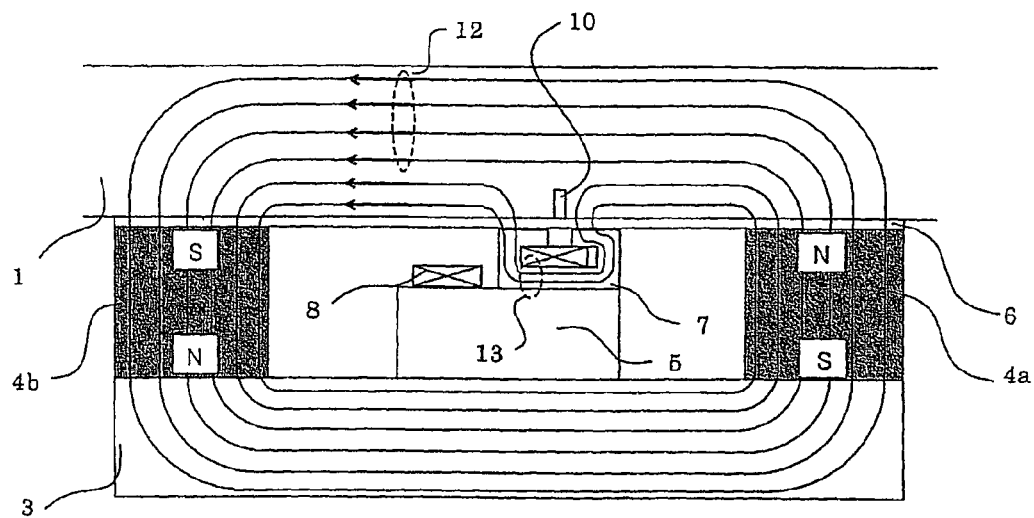
FIG. 16 is a configuration diagram illustrating a wire-rope flaw detector according to Embodiment 2.
Figure 17:
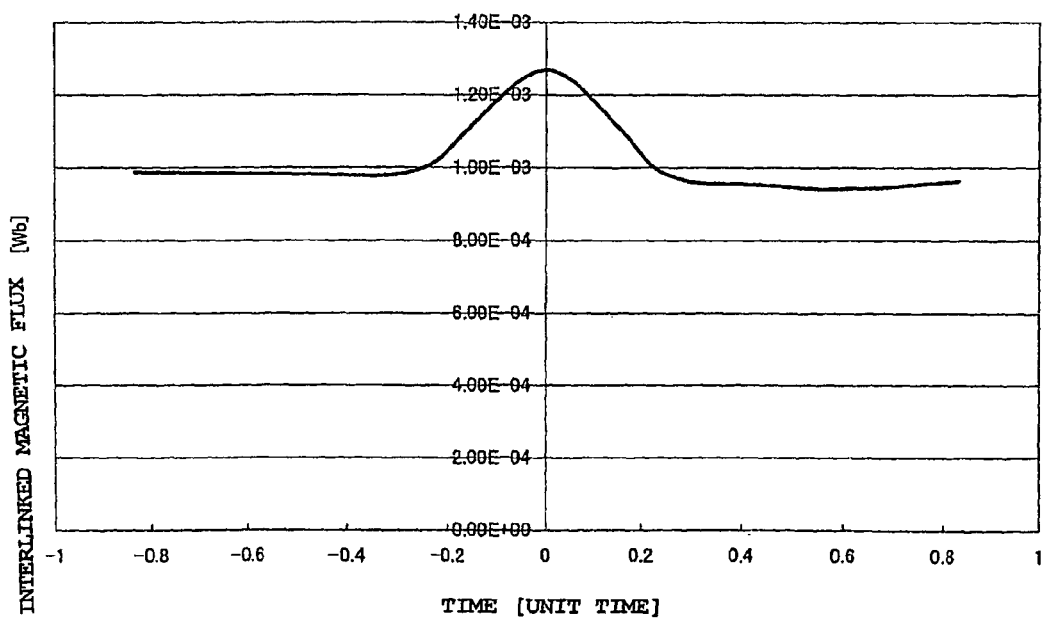
FIG. 17 is a waveform chart representing the amount of magnetic flux that is interlinked with the detection coil, when a flaw portion in Embodiment 2 passes by the flaw detection unit.
Figure 18:
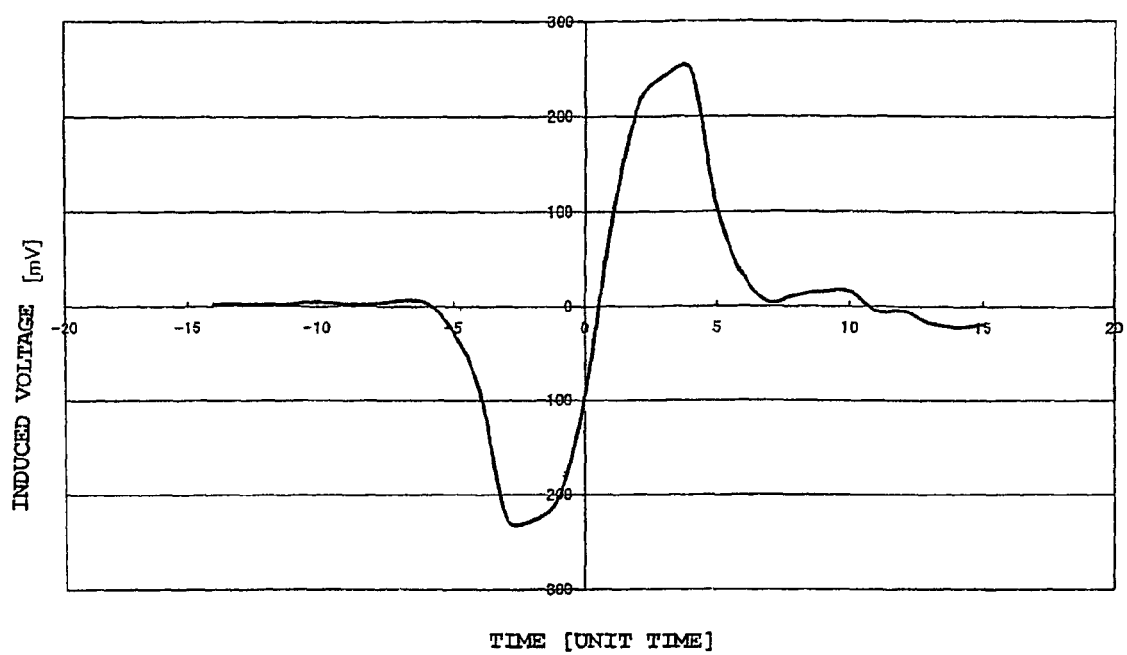
FIG. 18 is a waveform chart representing the waveform of a voltage induced across the detection coil in Embodiment 2.
Figure 19:
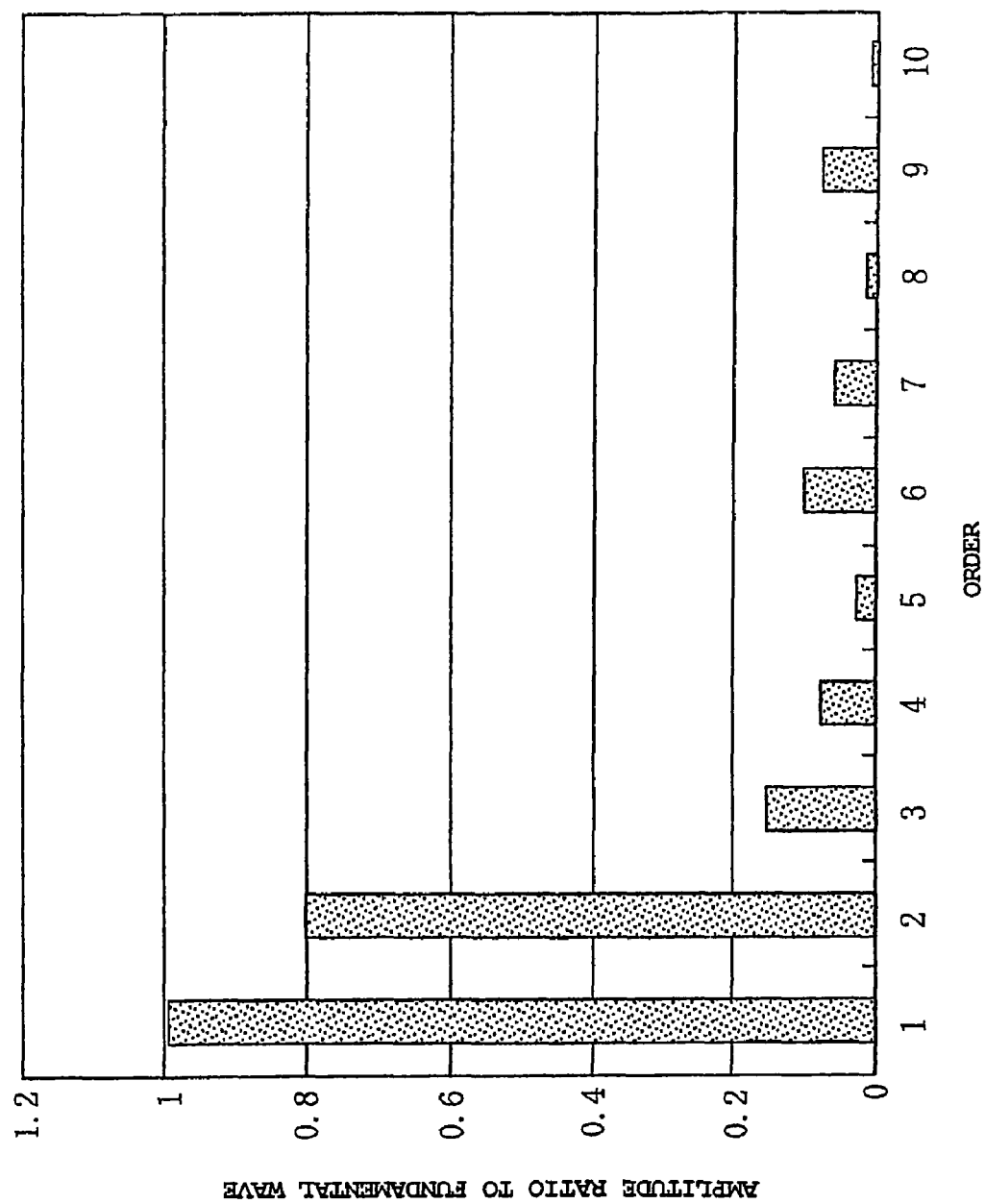
FIG. 19 is a graph representing the result of a frequency analysis on the waveform in FIG. 18.

FIG. 16 is a configuration diagram illustrating a wire-rope flaw detector according to Embodiment 2; the configuration diagram illustrates the flow of magnetic flux in the vicinity of a flaw portion in the wire rope 1 in the case where the wire-rope flaw detector is sliced along a plane including the center axis of the wire rope 1. FIG. 17 is a waveform chart representing the amount of magnetic flux that is interlinked with the detection coil 8, when a flaw portion passes by the flaw detection unit. FIG. 18 is a waveform chart representing the waveform of a voltage induced across the detection coil 8; FIG. 19 is a graph representing the result of a frequency analysis on the waveform in FIG. 18.

In Embodiment 2, as illustrated in FIG. 16, there may be utilized a magnetic circuit member 7 having a cross section in which the ferromagnetic material utilized therefor is approximately half of the ferromagnetic material utilized in Embodiment 1. In this situation, the voltage induced across the detection coil 8 has a waveform represented in FIG. 18; as can be seen from the result of a frequency analysis in FIG. 19, the waveform is characterized in that harmonics components whose amount is twice as large as that of the fundamental component are superimposed on the fundamental component. Because the usage amount of a magnetic circuit material is halved, Embodiment 2 can further reduce the production cost.

Embodiment 3

Figure 20:
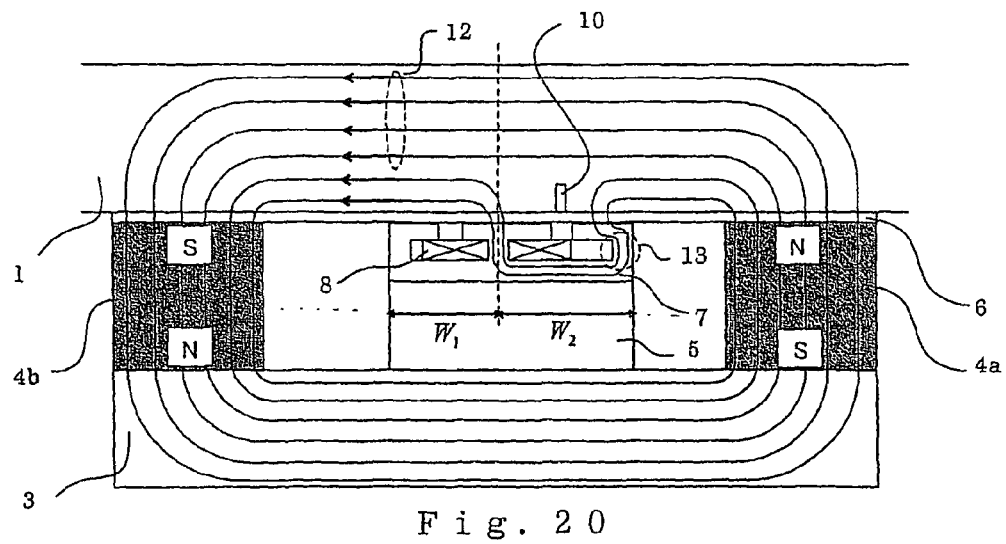
FIG. 20 is a configuration diagram illustrating a wire-rope flaw detector according to Embodiment 3.
Figure 21:
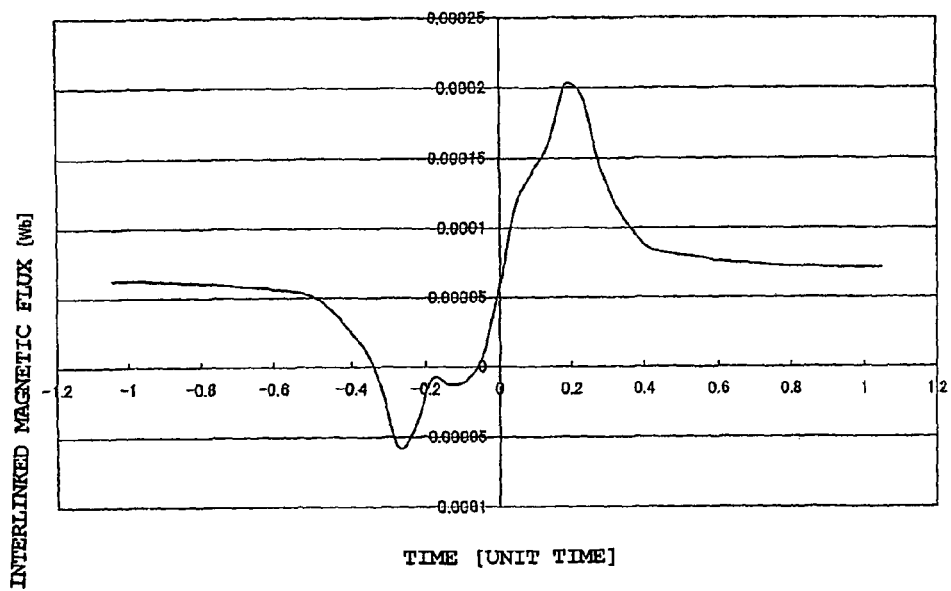
FIG. 21 is a waveform chart representing the amount of magnetic flux that is interlinked with the detection coil, when a flaw portion in Embodiment 3 passes by the flaw detection unit.
Figure 22:
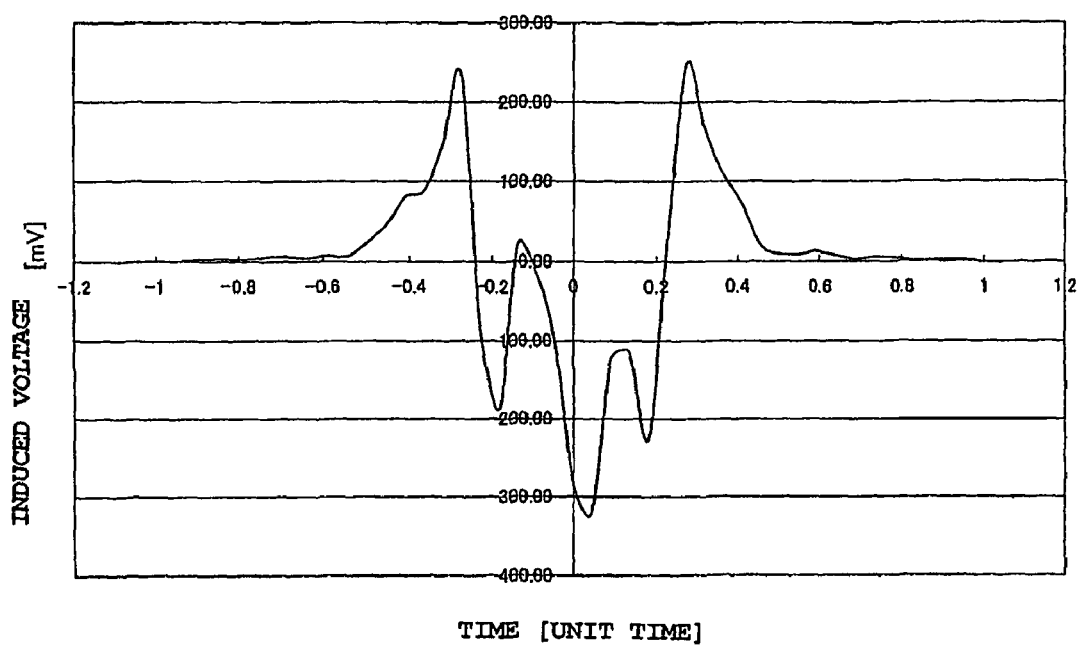
FIG. 22 is a waveform chart representing the waveform of a voltage induced across the detection coil in Embodiment 3.
Figure 23:
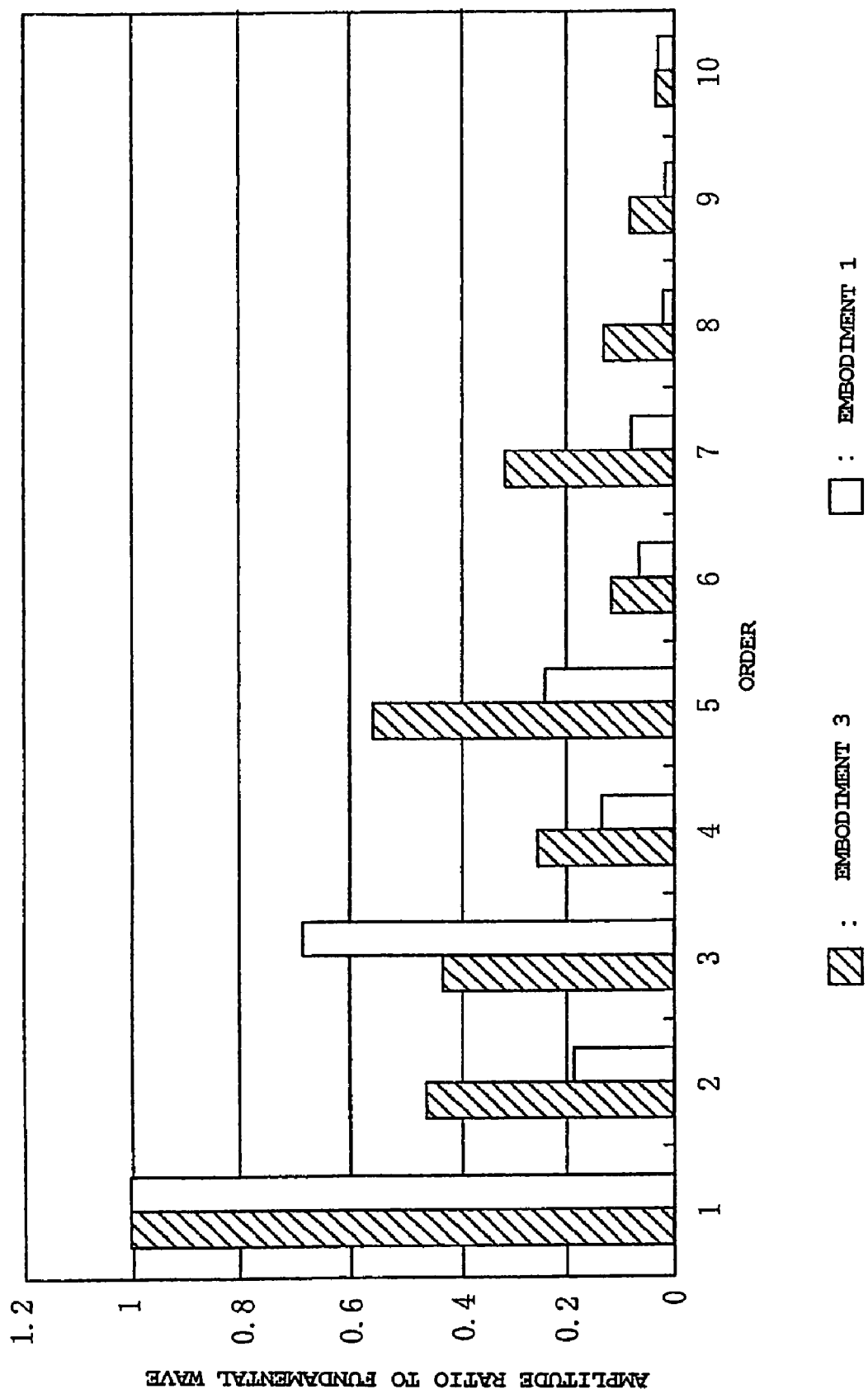
FIG. 23 is a graph representing the result of a frequency analysis on the waveform in FIG. 22.

FIG. 20 is a configuration diagram illustrating a wire-rope flaw detector according to Embodiment 3; the configuration diagram illustrates the flow of magnetic flux in the vicinity of a flaw portion in the wire rope 1 in the case where the wire-rope flaw detector is sliced along a plane including the center axis of the wire rope 1. FIG. 21 is a waveform chart representing the amount of magnetic flux that is interlinked with the detection coil 8, when a flaw portion passes by the flaw detection unit. FIG. 22 is a waveform chart representing the waveform of a voltage induced across the detection coil 8; FIG. 23 is a graph representing the results of a frequency analysis on the waveform in FIG. 22.

In Embodiment 3, the shape of a cross section of the magnetic circuit member according to Embodiment 1 is changed to a shape that is asymmetric with respect to the center of the detection coil 8, and $W_1<W_2$. By adopting the foregoing cross-sectional shape, the time from a time instant when a flaw portion approaches the flaw detection unit to a time instant when the flaw portion reaches the center of the detection coil 8 and the time in which the flaw portion travels from the center of the detection coil 8 and completely passes by the flaw detection unit are different from each other, whereby the frequency of a voltage induced during the former time and the frequency of a voltage induced during the latter time are different from each other; therefore, when harmonic waves thereof are considered, an induced voltage in Embodiment 3 includes more harmonic waves than an induced voltage in Embodiment 1 includes, whereby the characteristics of a waveform as a reference waveform becomes conspicuous; thus, the induced voltage can readily be distinguished from noise components, whereby Embodiment 3 can contribute to improvement of the signal-to-noise ratio. In an example represented in FIG. 23, even though the amplitude of the third harmonic wave is smaller than that in Embodiment 1, the respective amplitudes of the second, fourth, fifth, sixth, seventh, eighth, and ninth harmonic waves are larger than those in Embodiment 1.

Embodiment 4

Figure 24:
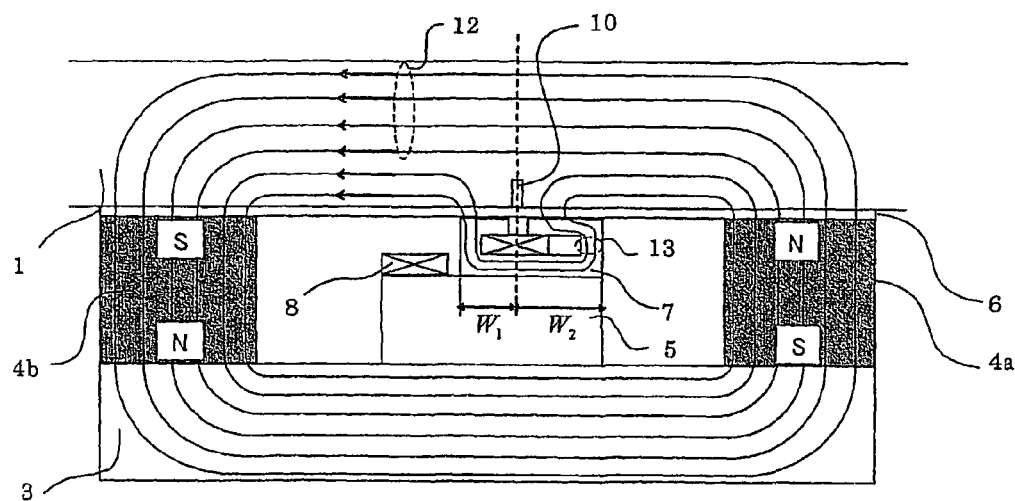
FIG. 24 is a configuration diagram illustrating a wire-rope flaw detector according to Embodiment 4.
Figure 25:
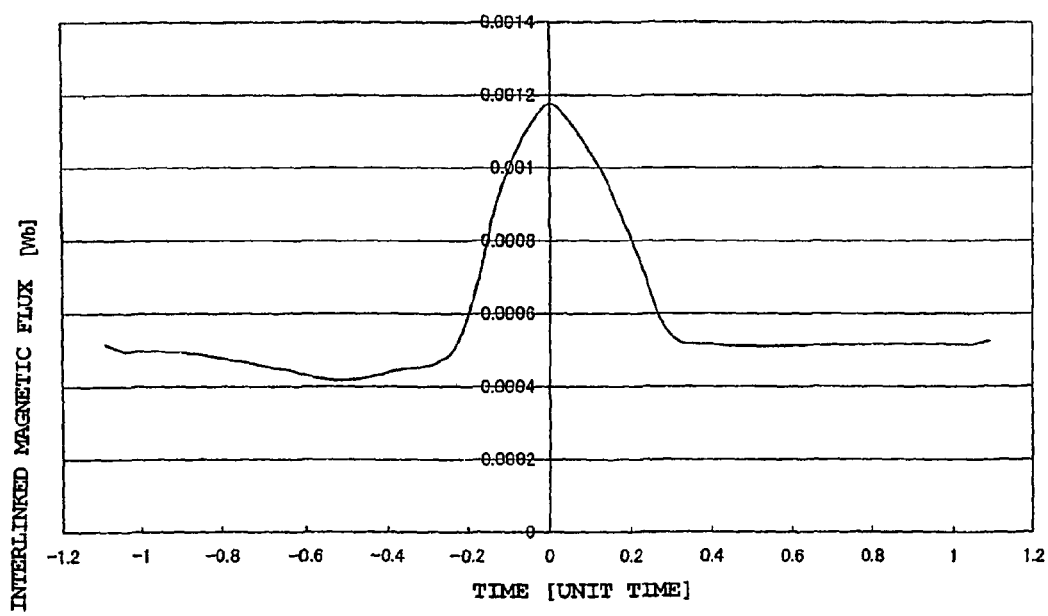
FIG. 25 is a waveform chart representing the amount of magnetic flux that is interlinked with the detection coil, when a flaw portion in Embodiment 4 passes by the flaw detection unit.
Figure 26:
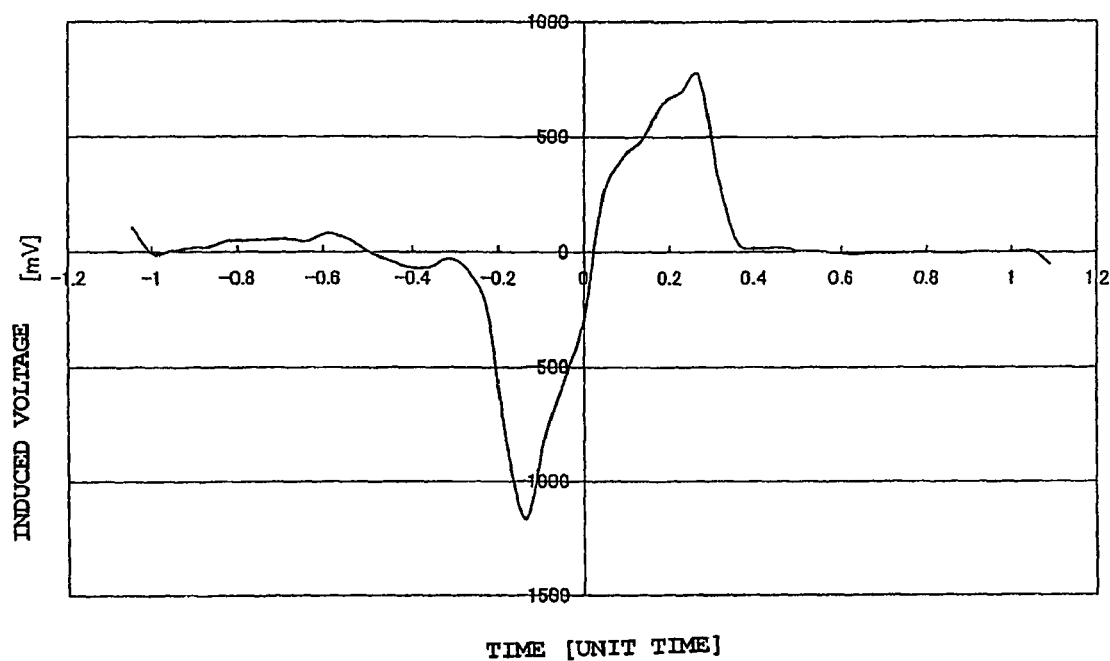
FIG. 26 is a waveform chart representing the waveform of a voltage induced across the detection coil in Embodiment 4.
Figure 27:
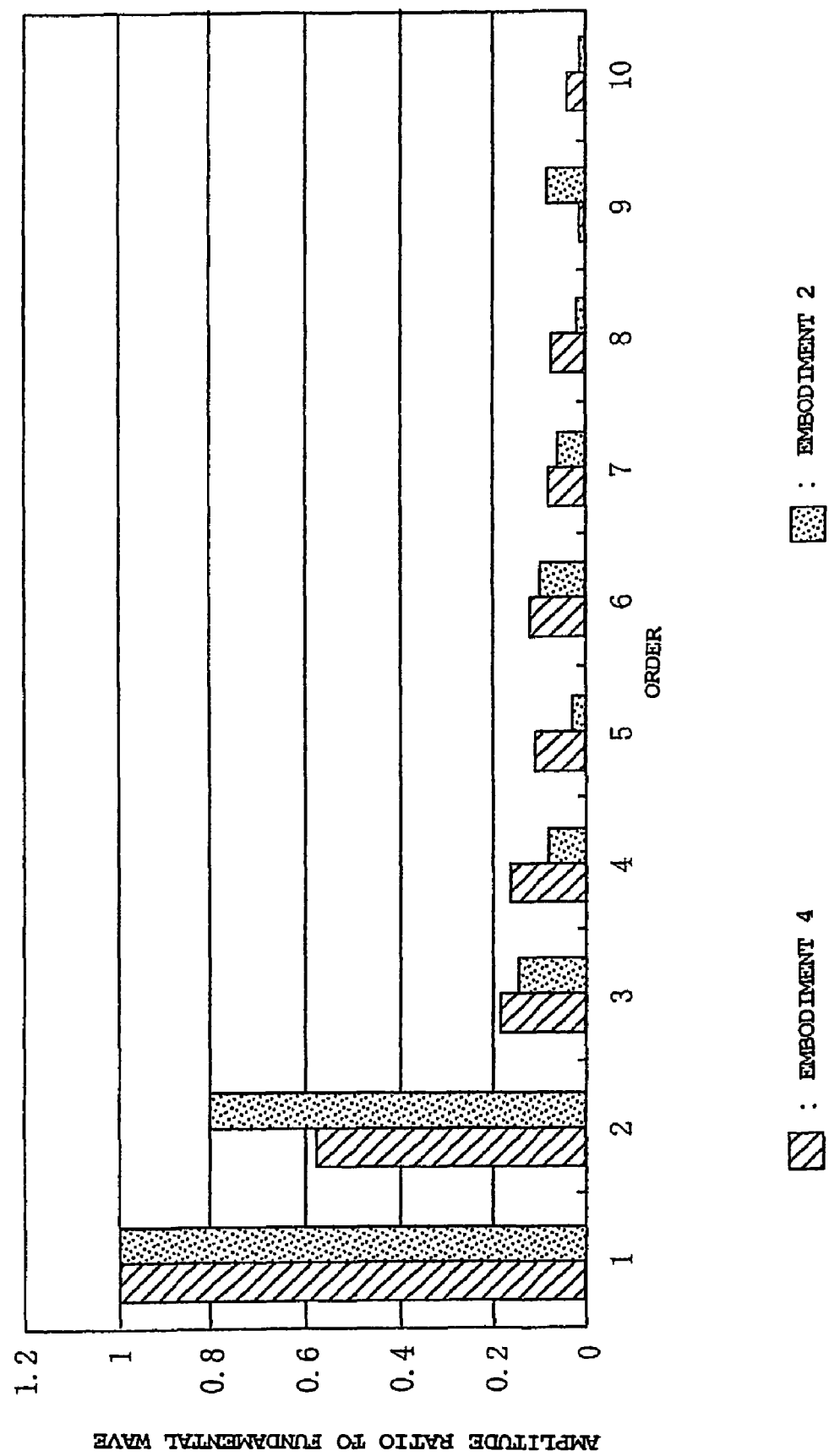
FIG. 27 is a graph representing the result of a frequency analysis on the waveform in FIG. 26.

FIG. 24 is a configuration diagram illustrating a wire-rope flaw detector according to Embodiment 4; the configuration diagram illustrates the flow of magnetic flux in the vicinity of a flaw portion in the wire rope 1 in the case where the wire-rope flaw detector is sliced along a plane including the center axis of the wire rope 1. FIG. 25 is a waveform chart representing the amount of magnetic flux that is interlinked with the detection coil 8, when a flaw portion passes by the flaw detection unit. FIG. 26 is a waveform chart representing the waveform of a voltage induced across the detection coil 8; FIG. 27 is a graph representing the results of a frequency analysis on the waveform in FIG. 26.

In Embodiment 4, the shape of a cross section of the magnetic circuit member according to Embodiment 2 is changed to a shape that is asymmetric with respect to the opening portion of the magnetic circuit member 7, and $W_1<W_2$. By adopting the foregoing shape, the time from a time instant when a flaw portion approaches the flaw detection unit to a time instant when the flaw portion reaches the opening portion and the time in which the flaw portion travels from the opening portion and completely passes by the flaw detection unit are different from each other, whereby the fundamental frequency of a voltage induced during the former time and the fundamental frequency of a voltage induced during the latter time are different from each other; therefore, when harmonic waves thereof are considered, an induced voltage in Embodiment 4 includes more harmonic waves than an induced voltage in Embodiment 2 includes, whereby the characteristics of a waveform as a reference waveform becomes conspicuous; thus, the induced voltage can readily be distinguished from noise components, whereby Embodiment 3 can contribute to improvement of the signal-to-noise ratio. In an example represented in FIG. 27, even though the amplitude of the third harmonic wave is smaller than that in Embodiment 2, the respective amplitudes of the third, fourth, fifth, sixth, seventh, and eighth harmonic waves are larger than those in Embodiment 2.

While the presently preferred embodiments of the present invention have been shown and described. It is to be understood that these disclosures are for the purpose of illustration and that various changes and modifications may be made without departing from the scope of the invention as set forth in the appended claims.

What is claimed is:

1. A wire-rope flaw detector comprising:
   a magnetizer that forms main magnetic flux in a predetermined section located along an axis direction of a wire rope; and
   a detection coil that detects, in the predetermined section, leakage magnetic flux emitted from a flaw portion of the wire rope,
   wherein a magnetic circuit member made of a ferromagnetic material intervenes in a magnetic circuit for leakage magnetic flux that is interlinked with the detection coil; and in a space where at least one of end portions, of the magnetic circuit member, that serve as an inflow port and an outflow port for the leakage magnetic flux is inserted between the detection coil and the wire rope, an opening portion extends in such a way as to intervene between the one end portion and the other end portion and is inserted between the detection coil and the wire rope.

2. The wire-rope flaw detector according to claim 1, wherein, in a space where at least one of end portions, of the magnetic circuit member, that serve as an inflow port and an outflow port for the leakage magnetic flux is inserted between the detection coil and the wire rope, the opening portion extends in such a way as to intervene between the one end portion and the other end portion and an mount of the extension is asymmetric with respect to the center of the detection coil.

3. The wire-rope flaw detector according to claim 1, wherein, in a space where at least one of end portions, of the magnetic circuit member, that serve as an inflow port and an outflow port for the leakage magnetic flux is inserted between the detection coil and the wire rope, the opening portion extends in such a way as to intervene between the one end portion and the other end portion and an mount of the extension is asymmetric with respect to the center of the opening portion of the magnetic circuit member.

4. The wire-rope flaw detector according to claim 1, wherein, in order to determine whether or not a flaw exists in the wire rope, there is outputted a degree of correlation between a voltage, which is measured, induced across the detection coil and a reference waveform created by preliminarily extracting frequency characteristics and phase characteristics typically included in the waveform of a voltage that is induced across the detection coil due to a flaw in the wire rope.

5. The wire-rope flaw detector according to claim 2, wherein, in order to determine whether or not a flaw exists in the wire rope, there is outputted a degree of correlation between a voltage, which is measured, induced across the detection coil and a reference waveform created by preliminarily extracting frequency characteristics and phase characteristics typically included in the waveform of a voltage that is induced across the detection coil due to a flaw in the wire rope.

6. The wire-rope flaw detector according to claim 3, wherein, in order to determine whether or not a flaw exists in the wire rope, there is outputted a degree of correlation between a voltage, which is measured, induced across the detection coil and a reference waveform created by preliminarily extracting frequency characteristics and phase characteristics typically included in the waveform of a voltage that is induced across the detection coil due to a flaw in the wire rope.

\* \* \* \* \*